United States Patent [19]
Tiffin

[11] Patent Number: 5,379,648
[45] Date of Patent: Jan. 10, 1995

[54] METHOD AND APPARATUS FOR TESTING CHEW-OUT STRENGTH OF PAPERBOARD CORE

[75] Inventor: Ronald C. Tiffin, Surrey, Canada
[73] Assignee: Sonoco Products Company, Hartsville, S.C.
[21] Appl. No.: 97,771
[22] Filed: Jul. 26, 1993
[51] Int. Cl.⁶ .......................................... G01N 3/00
[52] U.S. Cl. .................................. 73/847; 73/841; 493/37
[58] Field of Search .............. 73/862.191, 847, 848, 73/859, 860, 841, 845, 862.23; 493/37; 173/181, 182, 183

[56] References Cited

U.S. PATENT DOCUMENTS

| | | |
|---|---|---|
| 926,513 | 6/1909 | Souther . |
| 1,962,604 | 6/1934 | Luerssen et al. . |
| 2,779,187 | 1/1957 | Stewart . |
| 3,112,643 | 12/1963 | Lanahan . |
| 3,662,591 | 5/1972 | Bons ........................ 73/848 |
| 3,797,304 | 3/1974 | Klinger . |
| 3,839,905 | 10/1974 | McCallen ................... 73/848 |
| 4,089,211 | 5/1978 | Vercellone et al. ........ 73/847 |
| 4,159,650 | 7/1979 | Maguire . |
| 4,235,093 | 11/1980 | Spall . |
| 4,601,198 | 7/1986 | Kolitsch ..................... 73/847 |
| 4,794,801 | 1/1989 | Andrews et al. .......... 73/847 |
| 4,819,488 | 4/1989 | Morel ........................ 73/845 |
| 4,958,522 | 9/1990 | McKinlay . |

FOREIGN PATENT DOCUMENTS

| | | |
|---|---|---|
| 19634 | 8/1969 | Japan . |
| 27235 | 8/1971 | Japan . |
| 42208 | 9/1986 | Japan . |

Primary Examiner—Richard E. Chilcot, Jr.
Assistant Examiner—R. Biegel
Attorney, Agent, or Firm—Bell, Seltzer, Park & Gibson

[57] ABSTRACT

The invention provides a method and apparatus for testing the chew-out strength of paperboard cores. The apparatus of the invention includes a clamping element for clamping a tubular core to prevent rotation thereof; a splined chuck element in the form of an axially tapered member having a plurality of circumferentially distributed splines for insertion into one end face of the core; and a means for applying increasing torque at a controlled rate to the splined chuck element. A measuring means measures the torque applied to the splined chuck element. In operation, increasing amounts of torque are applied by the torquing means until the splined chuck element shears the end face of the tube resulting in chew-out of the core. The maximum torque force applied to the splined chuck element provides an accurate indication of the chew-out strength of the core.

21 Claims, 3 Drawing Sheets

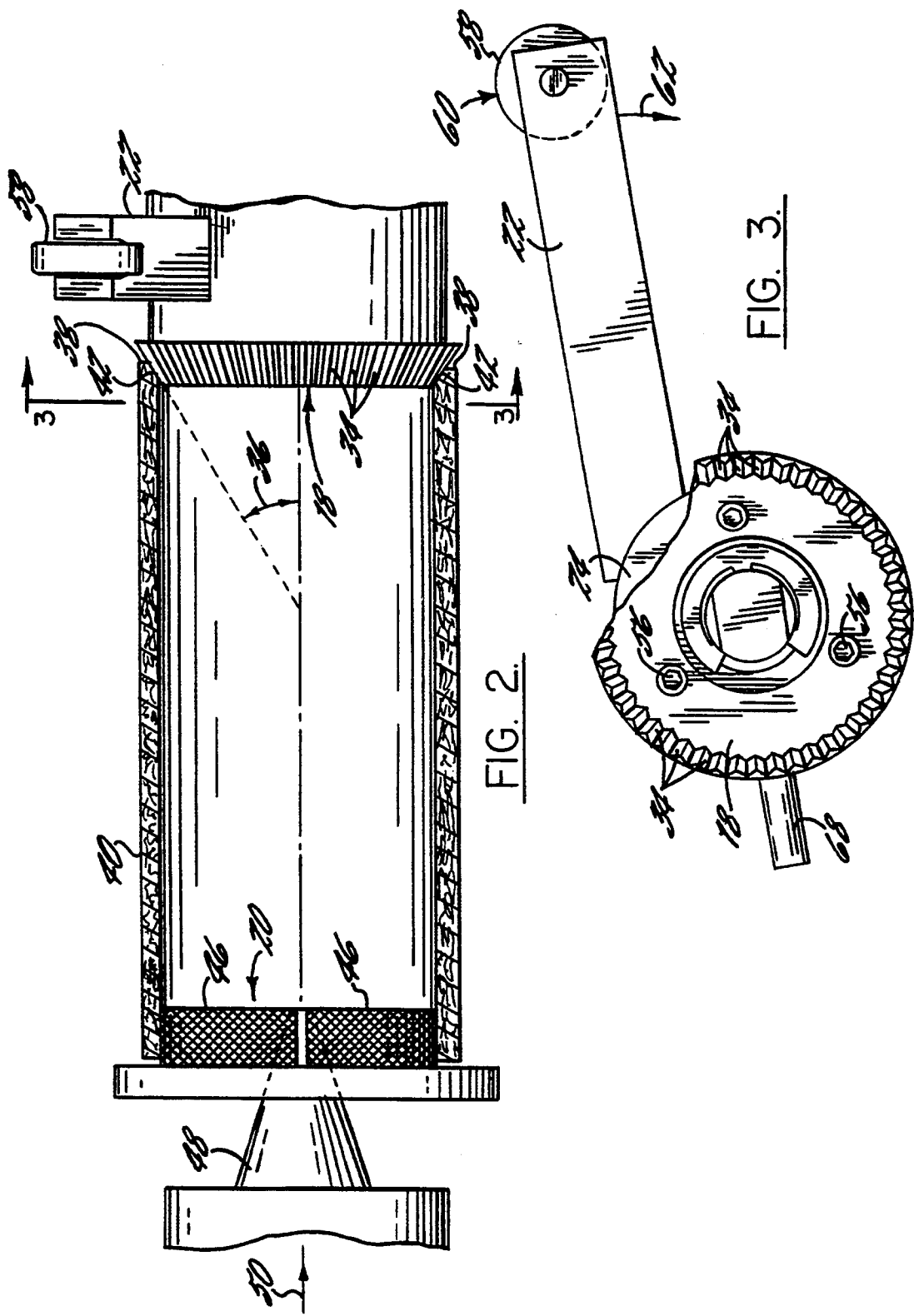

METHOD AND APPARATUS FOR TESTING CHEW-OUT STRENGTH OF PAPERBOARD CORE

FIELD OF THE INVENTION

The invention relates to a method and apparatus for evaluating the resistance to so-called "chew-out" strength of the ends of paperboard cores. More specifically, the invention is directed to a method and apparatus useful in evaluating the capability of the ends of paperboard cores to withstand torque applied to the end faces thereof by splined chucks which are engaged into the end faces of the tube during various winding operations.

BACKGROUND OF THE INVENTION

Wound paper tubes, or cores, are widely used in industry for winding and supporting film, textile material, paper and the like. These tubes are typically spirally wound tubes, although convolute wound tubes are also used to achieve these functions. Winding apparatus used to support the tubes during winding and unwinding operations normally employ two independent chucks that grip the core at each of its opposed ends by means of various chuck systems.

For heavy duty uses, such as for winding and unwinding for newspaper and Rotogravure Printing, the tubes can be very long, for example, up to about 10 feet (3.08 m) for U.S. Rotogravure Printing and 10.5 feet (3.22 m) for European Rotogravure Printing. In view of the large size, these tubes must be very heavy and strong in order to be able to carry the weight of a large roll of paper. In addition, the ends of the tube which are engaged by various chuck systems must also be very strong in order to withstand the torque applied to the tube ends during the wind and unwind operations.

One common type of chuck employed in winding operations for paper is a splined chuck which supports the core axially and also functions to prevent the core from slipping on the chuck when torque is applied. Typically, these chucks have a frustoconical exterior shape and there are a plurality of circumferentially distributed, axially elongate splines on the outer surface of the chuck. The core is mounted onto the chuck by partial insertion of the chuck axially into the end of the paperboard core. The chuck is inserted into the core employing a predetermined amount of axial force so that the axially elongate splines on the face of the chuck are positively engaged with and embedded into the paperboard core end faces and the adjacent interior peripheral surfaces thereof.

Typically, the rotation of the roll of paper material is achieved by means of a drive roll which contacts the face of the paper roll for rotation thereof. During the winding and unwinding operations, the rolls of material are often subjected to substantial circumferential acceleration and deceleration by the winding machines. This, in turn, subjects the engaged ends of the paperboard roll to substantial torque forces. If the tube construction and the resultant strength thereof are deficient, the chuck engaged into the tube end can tear the paperboard materials, resulting in "chew-out" of the tube ends. In such event, the tube ends are no longer positively engaged by the splined chuck.

Various testing apparatus have been used by core manufacturers and users to evaluate various properties of tubular cores. For example, spiral delamination strength of tubular cores has been measured in the industry by employing metal end caps on the tubular cores together with special chucks which firmly hold the core in place during testing. An electric motor and speed reducing transmission apply torque to the core until the core spirally delaminates. This in turn allows both core manufacturers and core users to evaluate spiral delamination strength of the core.

However, spiral delamination strength is only one parameter of core strength. Typically, when paperboard cores are supported by splined chucks, the paper at the core/chuck interface will shear and the chucks will chew-out the core prior to a spiral delamination of the entire core. Thus, the "chew-out strength" is typically the limiting parameter for the amount of torque that can be applied to paperboard cores when mounted on splined chucks.

There is, however, no commercially available device for accurately testing the chew-out strength of paperboard cores. Thus, neither core manufacturers nor core users can accurately evaluate chew-out properties of paperboard cores other than by actual use of the paperboard cores in the manufacturing environment. As a result, it can be necessary for a manufacturer to overdesign paperboard cores so that the chew-out strength is much greater than actually needed, on the one hand, while on the other hand, core users and purchasers cannot accurately evaluate a chew-out strength properties of cores prior to the actual use thereof.

SUMMARY OF THE INVENTION

The invention provides a chew-out test apparatus for paperboard cores which is simple in construction and can be readily used by individuals of both high and low mechanical skill. The chew-out test method and apparatus of the invention provides reliable and repeatable results so that chew-out strength properties of various paperboard constructions can be readily compared to each other. In preferred embodiments, the chew-out test apparatus of the invention is adapted for use with various commercially available materials testing apparatus of the type employing a conventional press for applying measured force and stress to materials. These press-type testing apparatus are widely available in industry and thus the investment in the chew-out tester of the invention can be minimized.

The apparatus of the invention for testing chew-out strength of tubular cores includes a means for clamping the core to prevent rotation of the core. A splined chuck element is provided for partial axial insertion into one end of the core. The splined chuck element is an axially tapered member, typically having a frustoconical shape, and includes a plurality of circumferentially distributed, axially elongate splines. Preferably, the splined chuck element is substantially identical to core chucks widely used in industry. An insertion means is provided for inserting the chuck into the core to positively engage the splines of the chuck into one end face of the core at a predetermined axial force. The apparatus also includes a torquing means for applying increasing torque at a controlled rate to the splined chuck element and a means for measuring the torque applied to the chuck element. In operation, increasing amounts of torque are applied by the torquing means at a controlled rate until the splined chuck element which is engaged with the end of the tube, shears the end face of the tube resulting in chew-out of the core. The torque force applied to the chuck element at the time of chew-out is measured and provides an accurate indication of the chew-out strength of the core.

In preferred embodiments of the invention, the splined chuck element has an axial taper of about 30 degrees. The clamping means is preferably an axially expandable chuck which is mounted on a frame coaxially with and spaced from the splined chuck element. A paperboard core of predetermined length is mounted between the splined chuck and the axially expanding clamping chuck. A first end of the tube is engaged onto the splined chuck element and the axially expandable clamping chuck is inserted into the second end of the core. The expandable clamping chuck is constructed for simultaneous radial expansion and axial movement so that as the expandable chuck is inserted into the second end of the tube it also applies axial force to force the tube onto the opposed splined chuck while at the same time applying a positive gripping contact to the interior periphery of the tube. Advantageously, the axially expandable chuck is applied to the second end of the tube body in combination with a means for applying a controlled insertion force thereto.

In one particularly advantageous embodiment of the invention, the chew-out test apparatus of the invention is adapted for use with a separate linear force applying and measuring means, which is preferably a press-type materials testing apparatus. Preferably, the means for applying controlled increasing torque to the splined chuck element includes a radially extending lever arm operatively engaged with the chuck so that the separate means for applying and measuring linear force can be applied to the end portion of the lever arm. Preferably, the splined chuck element and the clamping chuck are supported by a frame which includes at least one elongate lower foot support oriented transversely to the tube axis and on the same side of the frame as the extending lever arm. The frame and extending lever arm can be placed between opposing platens of a commonly available materials testing press of the type normally employed for testing materials. As the platens of the press are moved inwardly together, controlled force is applied to the radially extending lever arm until the splined chuck shears the engaged face of the paperboard core and rotates freely therein. Force measurement and recording means normally associated with the materials testing press measures and records the maximum torquing force applied to the splined chuck element during the test cycle.

BRIEF DESCRIPTION OF THE DRAWINGS

In the drawings which form a portion of the original disclosure of the invention:

FIG. 1 is a top perspective view of one preferred apparatus embodiment of the invention showing the apparatus in an unloaded form and positioned between opposed platens of a materials testing press or the like;

FIG. 2 is a fragmentary, partially schematic front view of the apparatus of FIG. 1 and additionally illustrating in cross section a paperboard tube mounted thereon;

FIG. 3 is a cross sectional view of the apparatus of FIG. 2 taken along line 3—3 thereof and illustrates a front plan view of the splined chuck element with a portion thereof broken away to illustrate connection of a lever arm thereto.

DETAILED DESCRIPTION OF THE PREFERRED EMBODIMENT

In the following detailed description, exemplary preferred embodiments of the invention are described to enable practice of the invention. It will be apparent that the terms used in describing the invention are used for the purpose of description and not for the purpose of limiting the invention to its preferred embodiments. It will also be apparent that the invention is susceptible to numerous variations modifications as will become apparent from a consideration of the invention as shown in the attached drawings and described herein.

Figure 1:
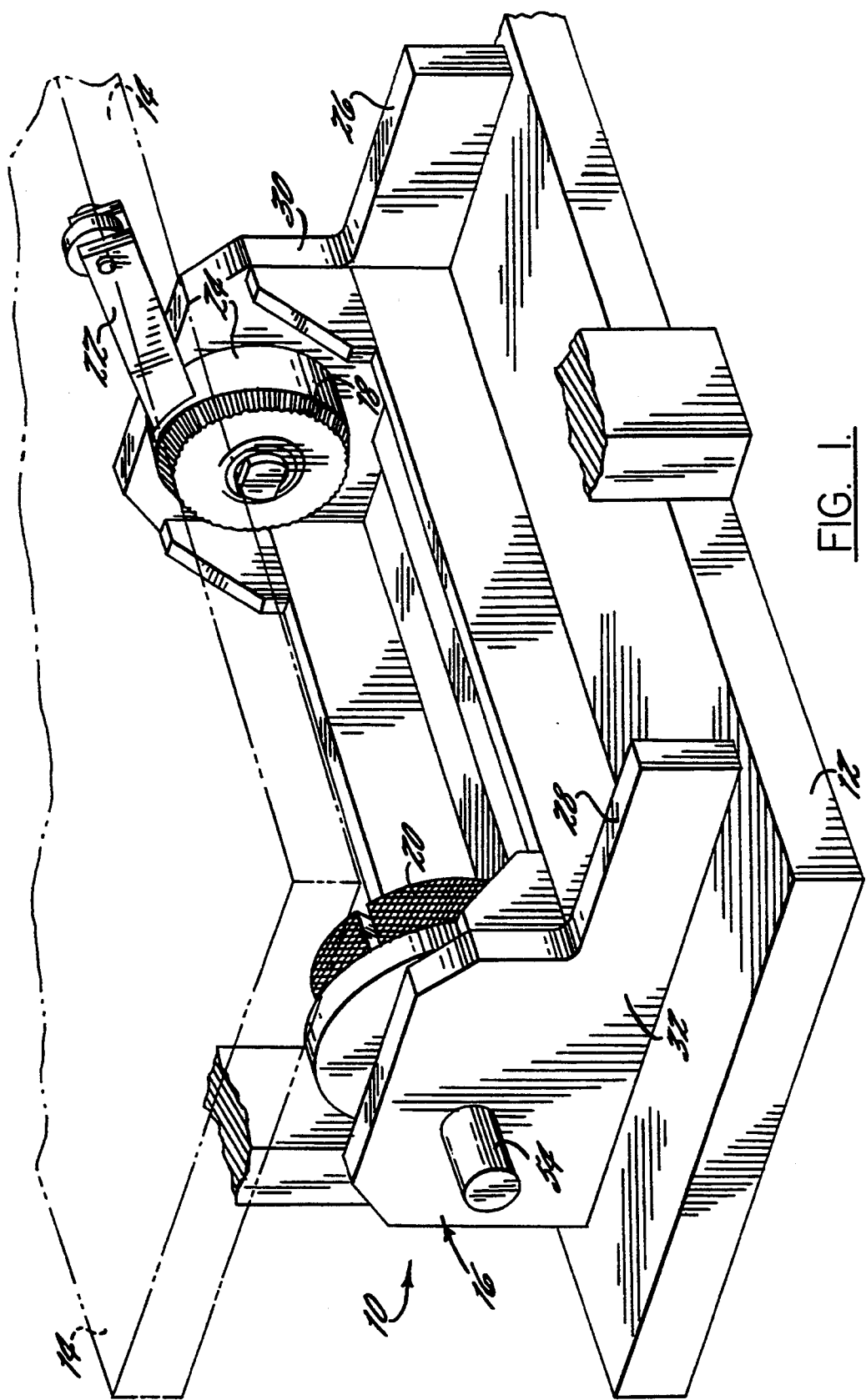

FIG. 1 illustrates one preferred construction for the apparatus 10 of the invention. As illustrated in FIG. 1, the apparatus 10 is shown supported between a lower platen 12 and an upper platen 14 of a press of the type commonly employed for testing tensile and compression properties of various materials. The apparatus includes a frame body 16 supporting both a splined chuck element 18 and a clamping member 20 which are arranged in opposed and spaced coaxial relationship. The splined chuck element 18 is rotatably mounted within the frame 16. A lever arm 22 is radially connected to the chuck member 18 a chuck mounting member 24 so that movement of the lever arm 22 results in rotation of the splined chuck 18.

As also seen in FIG. 1, the frame body 16 includes two elongate foot supports 26 and 28 which function to support the frame on the surface of platen 12 or the like and which also support the frame body 16 against rotation when substantial downward force is applied to lever arm 22. Advantageously, foot supports 26 and 28 are integrally formed with respective end members 30 and 32 which, in turn, support the clamping chuck 20 and the splined chuck element 18.

As best seen in FIGS. 2 and 3 the splined chuck element 18 includes a plurality of axially elongate triangularly shaped splines 34 on the exterior surface thereof. The splines 34 are distributed circumferentially around the exterior surface of the chuck member 18. The exterior surface of the chuck member is axially inclined at an angle 36 which is preferably between about 15° and about 60°, more preferably between about 20° and about 40°, advantageously about 30°. Preferably, the exterior surface of chuck 18 is substantially frustoconical in shape as illustrated in FIG. 2.

Because of the axial inclination of the exterior surface of chuck 18 as illustrated in FIG. 2, the exterior splines on the chuck 18 engage and embed into a portion of the end face 38 of tubular core 40 and also into a portion 42 of the inside peripheral surface of the tube body 40 adjacent the end face 38 thereof.

A preferred clamping means in the form of an radially expandable chuck member 20 is also illustrated in FIG. 2. The radially expandable chuck member includes a plurality of cooperating chuck portions 46 which, in turn, are supported for radial movement on frustoconical member 48. Inward axial movement of frustoconical member 48 in the direction indicated by arrow 50 results in radial outward movement of each of members 46 thereby radially expanding the chuck 20 for gripping of a portion of the interior surface 52 of the core body 40. In addition, the axial inward movement in the direction of arrow 50 of the frustoconical member 48 exerts axial force on the core body 40 which, in turn, engages the opposed end face 38 of the tubular body on splined chuck member 18.

It is important that the radially expandable chuck member 20 be mounted in frame body 16 (FIG. 1) such that the chuck member 20 is circumferentially fixed with respect to the frame body 16. This can be readily accomplished in any of various ways including the provision of one or more keys and keyways (not shown) connecting shaft 54 (FIG. 1) of frustoconical member 48 with end member 32 of the frame body 16. In addition, various keys and key ways (not shown) are also employed to connect each of chuck members 46 with frustoconical member 48 such that the radially outwardly moving members 46 are circumferentially fixed with respect to the frustoconical member 48.

As best seen in FIG. 3, a lever arm 22 is operatively attached to splined chuck member 18 via a support member 24 by bolts 56 or the like. The lever arm 22 extends generally radially outwardly from the splined chuck 18 and includes a rotatable cylindrical member 58 mounted adjacent the end thereof. Downwardly applied force onto cylindrical member 58 as indicated by arrow 60 results in pivoting motion of lever arm 22 in the direction indicated by arrow 62 which in turn imparts rotational force, i.e. torque, to the splined chuck element 18 in the direction indicated by arrow 64. Optional stub shaft 68 shown in FIG. 3 can be provided for interaction with the frame body 16 (FIG. 1) to keep the lever arm/chuck assembly from rotating either upwardly or downwardly beyond certain specified points.

Returning to FIG. 1, it will be seen that the lever arm 22 is of a length sufficient for extending above the top of the frame, i.e., above end members 30 and 32. This allows the lever arm 22 to be forced downwardly by the top platen 14 of a press while the apparatus is supported on the lower platen. It will be apparent that other means extending outwardly of the frame can be provided outwardly of the frame for receiving linear force from a platen or the like. Such means can be operatively connected to the splined chuck element 18 for rotation thereof by various gearing, hydraulic or similar arrangements and provide for the application of torquing force to the splined chuck element 18 from a separate force applying means.

Figure 4:
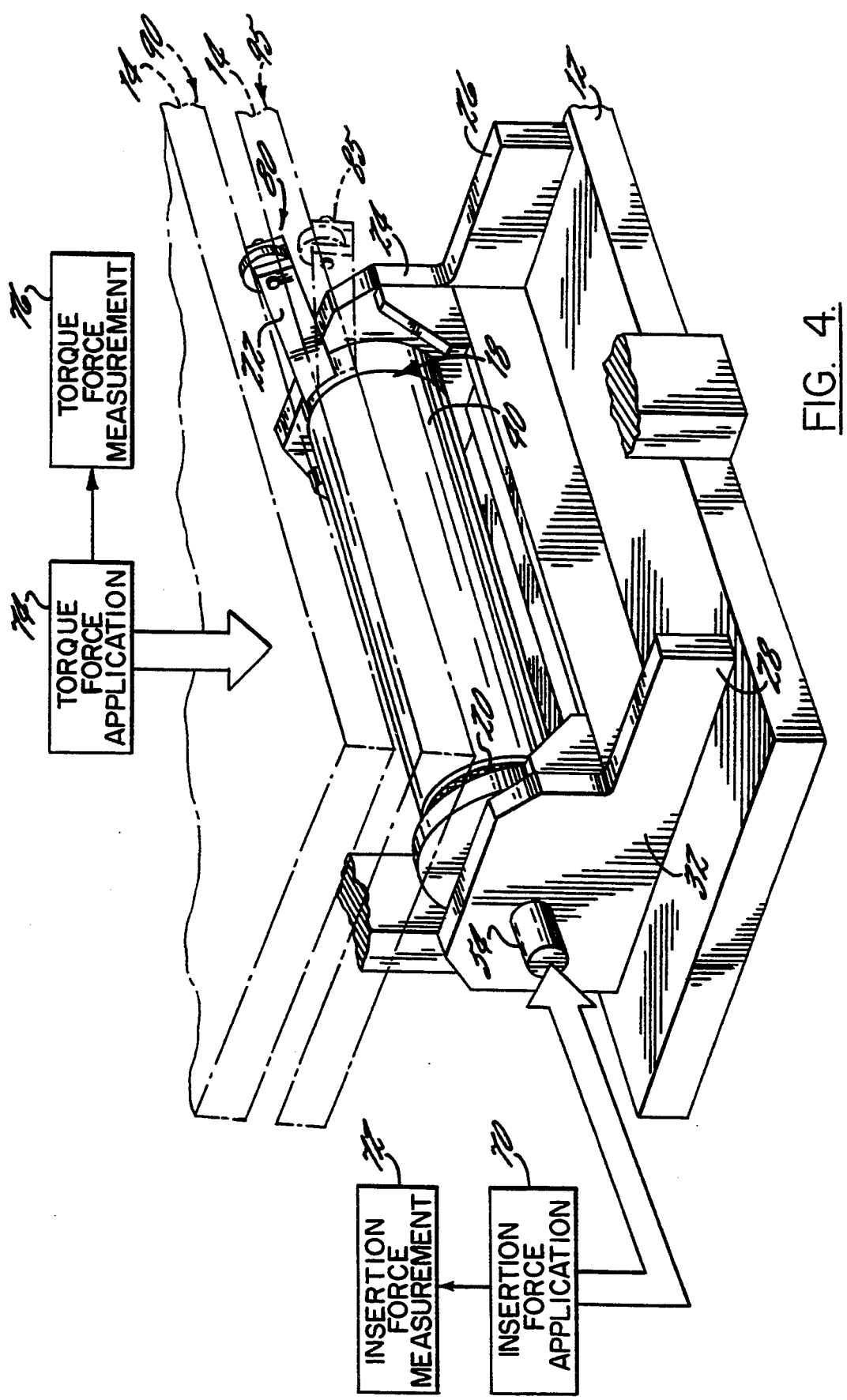
FIG. 4 is a perspective view of the apparatus of FIG. 1 and having a tube to be tested loaded therein, the apparatus being shown in position between two opposed platens of a materials testing apparatus in a first test initiation position and in a second test completion position.

Operation of the apparatus 10 is best seen in FIG. 4. Tube 40 is initially mounted adjacent splined chuck element 18 and coaxially opposed clamping chuck 20. A controlled inward axial force is applied via a force application means 70 to shaft 54 for inward axial movement thereof with resulting radial outward expansion of chuck 20 and the application of axial force to tube body 40 as discussed earlier. Advantageously, the insertion force application means 70 can be achieved by a hand pumped hydraulic system equipped with a force measurement means 72. Sufficient force is applied to rod member 54 to bury the splined chuck 18 into the face of the core body 40. It will be apparent to the skilled artisan that the axial insertion force must be kept substantially constant from test to test in order that results among tests be comparable. An insertion force of approximately 2,000 pounds per sq. in. has been found suitable for use with the embodiment of the invention illustrated in FIGS. 1-4 and using a hand pumped hydraulic press. However, it will be apparent that other mechanical or electrical force application means can be employed in the invention in place of the hydraulic pump for providing insertion force.

Once the tube has been sufficiently clamped and the splined chuck suitably engaged with the test face of the core body, a controlled force is applied via torque force application means 74 to the upper platen 14 of the press. The downward force on platen 14 imparts downward force to lever arm 22 which in turn imparts torque to splined chuck 18. A continuously increasing force is applied to lever arm 22 until the end face of the tube 40 is torn by the splined chuck 18 resulting in substantially free movement of lever arm 22. During the test the lever arm moves downwardly from a first upper position 80 to a final lower position 85. Similarly, during the test, upper platen 14 is moved from an upper position 90 to a final position 95. A torque force measurement means such as a gauge or digital read-out 76 records the maximum force applied to platen 14 during the test. The measured force is representative of the chew-out resistance of tube 40.

The following standard protocol has been employed in operating the embodiment of the invention illustrated in FIGS. 1-4 hereof. A commercially available press-type materials testing apparatus is set to have a maximum platen travel of 1.0 inch. The resolution for the force measuring means incorporated into the apparatus is set at pounds per inch. The top platen of the testing apparatus is raised sufficiently that the testing apparatus of the invention, 10, can be inserted between the opposed top and bottom platens. The test apparatus 10 is inserted between the platens and inspected to ensure that the bottom feet 26 and 28 are resting squarely on the bottom platen. Next, the lever arm 22 is manually moved to ensure that the splined chuck 18 rotates freely. A hydraulic line from a hand operated pump is then operatively connected to a hydraulic ram for applying force to shaft 54. The top platen 14 is then moved closely adjacent to the top or the lever arm and a tubular core sample having a length of 4.5 inches is placed between splined chuck element 18 and clamping chuck 20. The hydraulic hand operated pump is brought to a pressure of 2,000 pounds per square inch and the pressure is held constant. The force measuring system associated with the platens 12 and 14 is set to zero and the test cycle is then started by initiating downward movement of top platen 14 by the application of force thereto. An operator observes the lever arm movement during the test cycle. If the lever arm does not move steadily, the test is aborted. When the lever arm has been moved sufficiently that the end face of the test sample 40 has been torn sufficiently to chew out the tube face, the recorded maximum force is observed and recorded.

It will be apparent that the invention is susceptible to numerous modifications and substitutions from the preferred embodiment illustrated and discussed above. For example, in the above-described apparatus, axial insertion force is applied to insert the splined chuck element 18 into the tubular core via an opposed clamping member 20. However, it will be apparent that axial insertion force can be applied to the chuck element 18, itself for insertion of the chuck member 18 into the tubular core.

Similarly, the gripping chuck 20 grips the tubular body 40 from the inside face periphery thereof. However, various clamping members for clamping the exterior of the tube can also be employed in the invention. The preferred apparatus of the invention can, as illustrated herein, employ force application means and force measurement means which are found in many commonly available press-type materials testing apparatus.

It will be apparent that this decreases costs associated with the apparatus of the invention. However, it will be also apparent to the skilled artisan that a torque force application means can readily be incorporated into the apparatus of the invention so that the testing device is a self-contained unit. Numerous other modifications and variations of the invention will also be apparent.

The invention has been described in considerable detail with reference to its preferred embodiments. However, as indicated previously, the invention is susceptible to numerous modifications, variations and substitutions without departure from the spirit and scope of the invention as described in the foregoing detailed description and defined in the appended claims.

That which is claimed is:

1. An apparatus for testing the chew-out strength of a tubular core having first and second opposed ends comprising:
    clamping means for clamping the core to prevent rotation thereof;
    a splined chuck element for partial axial insertion into one end of the core comprising an axially tapered member having a plurality of axially elongate splines distributed circumferentially on the exterior surface thereof;
    insertion means for inserting the splined chuck element into the core to positively engage and embed the splines of the splined chuck element into the first end face of the core at a predetermined axial force;
    torquing means for applying increasing torque at a controlled rate to the splined chuck element; and
    means for measuring a force representative of the torque applied to the splined chuck element.

2. The apparatus of claim 1 additionally comprising a frame for supporting said splined chuck element and wherein said clamping means is supported by said frame in a position coaxial with and spaced from said splined chuck element.

3. The apparatus of claim 2 wherein said clamping means comprises a radially expandable chuck for insertion into the second end of said tubular core for gripping the interior periphery thereof.

4. The apparatus of claim 3 wherein said radially expandable chuck is adapted and arranged on said frame for axial movement in the direction of said splined chuck element and for simultaneous radial expansion during said axial movement.

5. The apparatus of claim 1 wherein said torquing means for applying increasing torque to said splined chuck element comprises a lever arm extending from said chuck in a radially outward direction.

6. The apparatus of claim 5 wherein said torquing means for applying increasing torque to said chuck additionally comprises a linear force application means for applying linear force to an end portion of said lever arm.

7. The apparatus of claim 6 additionally comprising a frame supporting said splined chuck element and said clamping means in opposed coaxial relationship, said frame means including at least one elongate foot element at a lower portion thereof and being oriented transversely to said splined chuck and said clamping means and being positioned on the same side of said frame as said radially outwardly extending lever arm.

8. The apparatus of claim 1 additionally comprising a frame means for supporting said clamping means and said splined chuck element in opposed coaxial relationship and wherein said insertion means for inserting said splined chuck element into said tubular core comprises a means for axially moving said clamping element in a direction toward said opposed splined chuck element.

9. The apparatus of claim 8 wherein said means for moving said clamping means in an axial direction toward said splined chuck element additionally comprises a means for measuring the axial force applied to said clamping means during the axial movement thereof.

10. An apparatus for testing the chew-out strength of a tubular core having first and second opposed ends and being adapted for use with linear force applying means and linear force measuring means comprising:
    clamping means for clamping the core to prevent rotation thereof;
    a splined chuck element for partial axial insertion into one end of the core comprising an axially tapered member having a plurality of axially elongate splines distributed circumferentially on the exterior surface thereof;
    insertion means for inserting the splined chuck element into the core to positively engage and embed the splines of the splined chuck element into the first end face of the core at a predetermined axial force;
    a frame for supporting said clamping means and said splined chuck element;
    torquing means for applying increasing torque at a controlled rate to the splined chuck element, at outwardly of said frame;
whereby said linear force applying means can apply force to said portion of said torquing means exterior of said frame and said force applied to said torquing means can be measured by said linear force measuring means.

11. The apparatus of claim 10 wherein said portion of said torquing means extending exterior of said frame is positioned for movement above an upper portion of said frame.

12. The apparatus of claim 11 wherein said portion of said torquing means exterior of said frame comprises an end portion of a lever arm having sufficient length for extending above the top of said frame.

13. The apparatus of claim 11 wherein said splined chuck element and said clamping means are coaxially supported by said frame in a spaced relationship.

14. The apparatus of claim 13 wherein said clamping means comprises a radially expandable chuck for insertion into the second end of said tubular core for gripping the interior periphery thereof.

15. The apparatus of claim 14 wherein said radially expandable chuck is adapted and arranged on said frame for axial movement in the direction of said splined chuck element and for simultaneous radial expansion during said axial movement.

16. The apparatus of claim 15 additionally comprising a means for axially moving said clamping element in a direction toward said coaxial splined chuck element and a means for measuring the force applied by said means for axially moving said clamping element.

17. A method for testing the chew-out strength of a tubular core having first and second opposed ends comprising:
    clamping said tubular core to prevent rotation thereof;
    positioning adjacent the first end of said clamped tubular core a splined chuck element comprising an axially tapered member including a plurality of circumferentially distributed axially elongate splines on the exterior surface thereof;

partially inserting said splined chuck element into said first end of said clamped tubular core sufficiently to positively engage and embed said splines of said splined chuck element into the end face of said first end of said clamped tubular core at a predetermined axially inward force;

applying increasing torque to said splined chuck element sufficiently to chew out a portion of the end face of said clamped tubular core; and measuring the maximum torque force applied to said splined chuck element during said applying step.

18. The method of claim 17 wherein said clamping step comprises gripping a portion of the interior periphery of said core.

19. The method of claim 17 wherein said inserting step comprises axially moving said tubular core toward said splined chuck element.

20. The method of claim 19 additionally comprising the step of measuring the axial force applied to said tubular core during said insertion step.

21. The method of claim 20 additionally comprising the step of providing a torque application element operatively associated with said splined chuck element for the transfer of force thereto, and applying a linear force to said torque application element to thereby apply torque to said splined chuck element.

* * * * *

UNITED STATES PATENT AND TRADEMARK OFFICE
CERTIFICATE OF CORRECTION

PATENT NO. : 5,379,648
DATED : January 10, 1995
INVENTOR(S) : Ronald C. Tiffin

It is certified that error appears in the above-identified patent and that said Letters Patent is hereby corrected as shown below:

Column 4, line 14, after "variations" insert -- and --.

Column 4, line 28, after "18" insert -- via --.

Column 6, line 36, "or" should be -- of --.

Column 8, line 30, after "at" insert -- least a portion of said torquing means extending --.

Signed and Sealed this

Seventh Day of March, 1995

Attest:

BRUCE LEHMAN

Attesting Officer       Commissioner of Patents and Trademarks